United States Patent
Sharma et al.

(10) Patent No.: US 11,491,002 B2
(45) Date of Patent: Nov. 8, 2022

(54) IMPLANTABLE CARDIO-VASCULAR FLOW STREAMLINER

(71) Applicant: Indian Institute of Technology Bombay, Mumbai (IN)

(72) Inventors: Shailendra Deendayal Sharma, Mumbai (IN); Sanjeev Dasrao Muskawad, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 162 days.

(21) Appl. No.: 15/235,442

(22) Filed: Aug. 12, 2016

(65) Prior Publication Data

US 2017/0042660 A1 Feb. 16, 2017

(30) Foreign Application Priority Data

Aug. 14, 2015 (IN) .......................... 3091/MUM/2015

(51) Int. Cl.
*A61F 2/06* (2013.01)
(52) U.S. Cl.
CPC .......... *A61F 2/06* (2013.01); *A61F 2002/068* (2013.01); *A61F 2250/0082* (2013.01)
(58) Field of Classification Search
CPC .................. A61F 2/06; A61F 2002/068; A61F 2250/0082
USPC .................................................. 623/1.1–1.48
See application file for complete search history.

(56) References Cited

U.S. PATENT DOCUMENTS

| | | | |
|---|---|---|---|
| 7,811,244 B2* | 10/2010 | Soerensen | A61F 2/06 137/597 |
| 9,066,997 B2* | 6/2015 | Ma | A61L 27/56 |
| 10,327,885 B2* | 6/2019 | Hoganson | A61F 2/022 |
| 11,045,300 B2* | 6/2021 | Kassab | A61B 5/1076 |
| 2015/0366651 A1* | 12/2015 | Hoganson | A61F 2/06 623/23.72 |
| 2018/0064525 A1* | 3/2018 | Frid | A61F 2/2412 |
| 2020/0222173 A1* | 7/2020 | Walzman | A61F 2/82 |
| 2021/0401565 A1* | 12/2021 | Kassab | A61M 1/3613 |

FOREIGN PATENT DOCUMENTS

GB 2382776 A * 6/2003 ............... F15D 1/04

* cited by examiner

*Primary Examiner* — Suzette J Gherbi

(57) ABSTRACT

Embodiments herein provide an implantable Flow Streamliner for passively regulating blood streams in a TCPC subject. The implantable Flow Streamliner is configured to split a blood stream from an Inferior Vena Cava (IVC) and a blood stream from a Superior Vena Cava (SVC), without a direct collision between the blood streams. Further, the implantable Flow Streamliner is configured to distribute the blood stream from the IVC containing hepatic nutrients in proportion to a Left Pulmonary Artery (LPA) and a Right Pulmonary Artery (RPA). Further, the implantable Flow Streamliner is configured to distribute the blood stream from the SVC in equal proportion to the LPA and the RPA.

13 Claims, 13 Drawing Sheets

IMPLANTABLE CARDIO-VASCULAR FLOW STREAMLINER

TECHNICAL FIELD

The present invention relates to implantable Flow Streamliner and more particularly related to an implantable Flow Streamliner for passive control of blood flow in desired direction with reduced energy loss in a patient. The present application is based on, and claims priority from an Indian Application Number 3091/MUM/2015 filed on 14 Aug. 2015 the disclosure of which is hereby incorporated by reference.

BACKGROUND OF INVENTION

In most cases of congenital heart disease, it is essential to improve pulmonary circulation. It is particularly desirable to maintain normal blood circulation to the lungs of the patient.

FIG. 1 is a schematic depicting a natural circulation of blood in a human body. Deoxygenated blood from the entire human body is received in the Right Atrium (RA) of a heart and supplied to the Right Ventricle (RV). The RV further pumps the blood into the lungs for oxygenation from where it is received in the Left Atrium (LA) of the heart. The oxygenated blood collected in the LA is then received in the Left Ventricle (LV) which further pumps it to the body thus completing the close circuit.

FIG. 2 is a schematic representing the blood circulation in the human body having congenital heart defect (CHD) with a single ventricle. In case of the congenital heart defect, the RV is malformed and both atria are interconnected due to a hole. As a result, the LV alone has to pump the mixture of the oxygenated blood and the deoxygenated blood to the lungs and to the body both. Further, the blood from the lungs and the body returns to the LA and the RA respectively, to complete the circuit in two parallel close loops.

In normal cardiovascular circulation the blood flows in a single close loop. RV and LV are anatomically separated by intervening partition, called as inter-ventricular septum. In this close loop of cardiovascular flow, the ventricles are separated by pulmonary and systemic vascular tree. When one of the ventricles is underdeveloped, the functional ventricle has to pump the blood in both systemic and pulmonary vasculature. This results in two parallel loops.

The probability of children born with CHD having only one effective ventricle is about 2 per 1000 births. In children with such birth defect, the single ventricle has to pump the blood simultaneously to the body as well as to the lungs. In these cases, the single ventricle is pumping into the systemic (body) and pulmonary (lungs) vascular network. This parallel circulation (across pulmonary and systemic vascular network) causes cyanosis which is a result of mixing of the oxygenated and the deoxygenated blood in the single ventricle. It also creates ventricular volume overload. Due to these reasons, the children with one effective ventricle need to be treated to increase the life expectancy. For the palliation of this kind of severe congenital heart problem, a surgical procedure is performed, called as Fontan surgery.

The Fontan surgery procedure involves correcting the congenital heart defect, wherein the inter-atrial septal hole is closed and the right atrium is connected directly to the pulmonary artery bypassing the right ventricle completely from the blood circulation circuit. Thus, the Fontan surgery prevents mixing of the oxygenated blood with the deoxygenated blood and also renders the circulation circuit in a single close loop. However, in the absence of the RV the blood supply from the body to the lungs becomes a passive process and hence possesses less kinetic energy. The blood circulation in the human body after a Fontan surgery is schematically shown in FIG. 3.

Sectional anatomies of a normal human heart and that of suffering from CHD are shown in FIGS. 4a and 4b, respectively. As shown, septum divides the heart vertically into left heart and right heart and each of them is further horizontally divided into atrium and ventricle with a non-return valve between them. Thus a heart has four chambers—Left Atrium (LA), Left Ventricle (LV), Right Atrium (RA) and Right Ventricle (RV). Deoxygenated blood from upper body (head and arms) and lower body (torso and legs) is carried to heart through Superior Vena Cava (SVC) and Inferior Vena Cava (IVC), and is collected in Right Atrium. From RA this blood is supplied through Tricuspid Valve (TV) to RV which pumps it through Pulmonary Valve (PV) to Left Pulmonary Artery (LPA) and Right Pulmonary Artery (RPA) leading to left and right lungs. Oxygenated blood from lungs returns to heart through Pulmonary Veins and gets collected in LA which pushes it through Mitral Valve (MV) into LV. Contraction of LV pumps oxygenated blood through Aortic Valve (AV) to highly curved Aorta whose branches supply it to the upper body and the lower body, thus completing the circuit of blood circulation. FIG. 4b shows a typical congenital heart defect wherein the RV is malformed and inter-atrial septum between RA and LA has a hole allowing mixing of oxygenated blood with deoxygenated blood. In this situation LV alone pumps the mixed blood to the body and to the lungs as well thereby causing continual deterioration of child's health, warranting an early Fontan surgery.

The surgery termed as "Total Cavo-Pulmonary Connection" (TCPC) is currently the most promising modification of a Fontan surgical repair (i.e., Fontan surgery) for single ventricle congenital heart disease. The TCPC involves a surgical connection of the SVC and the IVC directly to the RPA, bypassing the right heart to create flow in series. The SVC and the IVC with a prosthetic tubular extension are always connected to the RPA owing to relatively shorter distance resulting in elongation of the LPA from the junction. Further, the pulmonary artery is severed along the dotted line (shown in FIG. 4b) from the T-joint between the RPA and the LPA, and both the open ends are then sutured to close. In the univentricular system, the ventricle experiences a workload which may be reduced by optimizing the cavae-to-pulmonary anastomosis. This palliative surgical procedure leads to a separation between the oxygenated and the deoxygenated blood, which is critical for effective oxygen transport to the human body. As a result of this modified blood circulation, the single ventricle experiences an increased workload, pumping the blood to both the systemic circulation and to the lungs.

The TCPC surgery is the most practiced Fontan operation which has two variants—Intracardiac TCPC and Extra cardiac TCPC as shown in FIGS. 5a and 5b, respectively. In TCPC surgery, a surgeon disconnects the SVC and the IVC from the RA of heart and joins them directly to the RPA to direct returning blood from the body to lungs. While the Intracardiac TCPC involves construction of a composite intra-atrial tunnel with the use of the posterior wall of the RA, the extracardiac TCPC involves extension of IVC using a prosthetic tube exterior to RA. Both the TCPC variants present a configuration in a simple form of a cross connection. As a result of this TCPC surgery, the blood streams flowing in opposite directions through the SVC and the IVC collide head on with each other and lose momentum thereby causing the loss of kinetic energy. In addition, an undesirable turbulence and unsteadiness are also created due to the collision between these blood streams as schematically represented in FIG. 6.

There exists a mechanism to minimize the impact of the collision of the SVC and the IVC blood streams, by providing an offset between the SVC and IVC axes as schematically shown in FIG. 7. As a result of the offset provided, a vortex is naturally formed due to shear between the opposite blood streams at the junction which facilitates smooth flow of blood to the lungs and a little energy is absorbed from the blood streams to sustain the rotation of the vortex. Further, due to the sharp corners at the joints of the SVC and the IVC with each of the pulmonary artery (i.e., RPA and LPA) cause blood flow separation which becomes additional source of energy loss. The overall energy loss due to vortex formation and blood flow separation is still less compared to the head on collision of the blood streams.

However, this surgical offset leads to lung developmental problems caused due to unequal IVC blood flow distribution. For example, depending on the extent of the offset, the blood streams choose their paths and create a bias for the IVC blood towards one of the lungs, thereby depriving the other lung of nutritive secretion that is provided by the liver to the IVC blood.

SUMMARY

The principal object of the embodiments herein is to provide an implantable Flow Streamliner for passively regulating blood streams in a subject for a TCPC surgery and also in a subject for corrective procedure for improving hemodynamics in old case of TCPC.

Another object of the embodiments herein is to provide the implantable Flow Streamliner for splitting a blood stream from an IVC and a blood stream from an SVC, without a collision between the blood streams.

Another object of the embodiments herein is to provide the implantable Flow Streamliner for distributing the blood stream from the IVC, containing hepatic nutrients, in appropriate proportion to the LPA and the RPA.

Another object of the embodiments herein is to provide the implantable Flow Streamliner for distributing the blood stream from the SVC in appropriate proportion to the LPA and the RPA.

Yet another object of the embodiments herein is to provide the implantable Flow Streamliner for facilitating natural growth of the blood vessels which is essential for the increasing blood supply of patients with their growing age.

Yet another object of the embodiments herein is to provide an implantable Flow Streamliner for appropriately guiding the flow of the IVC blood carrying hepatic contents to both the lungs depending on impedance offered by each pulmonary vascular tree.

Yet another object of the embodiments herein is to provide the implantable Flow Streamliner to enable confluence of streams of the SVC and the IVC blood with minimal shear between the streams based on accurate placement of the implantable Flow Streamliner in the pulmonary artery.

Yet another object of the embodiments herein is to provide the implantable Flow Streamliner for corrective procedure in an old case of the TCPC to suppress the vortex formation due to an offset between the SVC and the IVC.

Yet another object of the embodiments herein is to provide the implantable Flow Streamliner to smoothly guide the blood from the IVC carrying hepatic nutrients to both the lungs in an old case of TCPC with any offset between the SVC and the IVC.

Yet another object of the embodiments herein is to provide the implantable Flow Streamliner to smoothly guide the blood from the SVC to both the lungs in an old case of TCPC with any offset between the SVC and the IVC.

Accordingly the embodiments herein provide an implantable Flow Streamliner for passively regulating blood streams in a TCPC subject. The implantable Flow Streamliner is configured to split a blood stream from an IVC and a blood stream from a SVC, and enable their confluence without a collision between the blood streams. Further, the implantable Flow Streamliner is configured to distribute the blood stream from the IVC, containing hepatic nutrients, in proportion to a LPA and a RPA. Further, the implantable Flow Streamliner is configured to distribute the blood stream from the SVC in proportion to the LPA and the RPA.

In an embodiment, the implantable Flow Streamliner is a cardio-vascular Flow Streamliner.

In an embodiment, the blood stream from the IVC, containing the hepatic nutrients, is regulated in proportion to the LPA and the RPA without constraint.

In an embodiment, the blood stream from the SVC is regulated in proportion to the LPA and the RPA without constraint.

In an embodiment, the implantable Flow Streamliner is configured to enable confluence of the blood streams from the SVC and the IVC to the RPA and the LPA.

In an embodiment, the implantable Flow Streamliner is positioned horizontally at about the mid-plane of the junction facing towards the IVC and the SVC, wherein the SVC and the IVC are connected with the RPA facing each other.

In an embodiment, the implantable Flow Streamliner is positioned vertically facing towards the LPA and the RPA, wherein the SVC and the IVC are connected with the RPA facing each other and the implantable Flow Streamliner is connected with the SVC and the IVC along their axes.

In an embodiment, the position of the implantable Flow Streamliner equalizes the velocity of the blood flow from the IVC and the velocity of the blood flow from the SVC at the LPA while leaving the implantable Flow Streamliner.

In an embodiment, the position of the implantable Flow Streamliner equalize the velocity of the blood flow from the IVC and the velocity of the blood flow from the SVC at the RPA while leaving the implantable Flow Streamliner.

In an embodiment, the SVC is connected with the RPA in a flared shaped to enable the blood stream turn smoothly in the RPA and the LPA.

In an embodiment, the IVC is connected with the RPA in a flared shaped to enable the blood stream turn smoothly in the LPA and the RPA.

In an embodiment, the implantable Flow Streamliner is derived from at least a tissue-engineered material, a biocompatible polymers, a biocompatible material, an auto graft, a homograft, and a heterograft.

In an embodiment, the implantable Flow Streamliner is constructed out of a thin sheet at least from soft, hard, rigid, a thin membrane, a flexible material, and a rigid material.

In an embodiment, the implantable Flow Streamliner is constructed as an integral part of an IVC graft.

In an embodiment, the implantable Flow Streamliner is constructed as an integral part of an SVC graft.

In an embodiment, the implantable Flow Streamliner is in at least one of a flat shape, a curved shape in two dimensions (2D) and a curved shape in three dimensions (3D).

In an embodiment, the blood streams from the IVC and from the SVC are enabled to co-flow with a minimal shear at their interface based on the position of the implantable Flow Streamliner at the junction of the SVC, the IVC, the LPA and the RPA.

In an embodiment, the Flow Streamliner has a curvilinear shape adapting to the offset between the SVC and the IVC so as to split the blood streams from the SVC and the IVC into two blood streams and guide them to the RPA and the LPA.

In an embodiment, the implantable Flow Streamliner eliminates bias of the blood streams from the SVC and the IVC, and directs the flow of the blood streams in proportion to the LPA and the RPA.

In an embodiment, the implantable Flow Streamliner corrects irregularity in the TCPC configuration in the form of at least one of dilation and stenosis creating flow abnormalities.

In an embodiment, the implantable Flow Streamliner is implanted by one of a routine surgery, minimally invasive surgery and a catheter-based intervention for correcting the flow abnormalities in old TCPC subjects.

In an embodiment, the implantable Flow Streamliner allows natural growth of the blood vessels which is essential for the increasing blood supply to the lungs of TCPC patients with their growing age.

In an embodiment, the implantable Flow Streamliner is implanted to reduce the energy loss and improves the cardio-vascular hemodynamics in TCPC subjects.

In an embodiment, the implantable Flow Streamliner is an integral component of the graft, simplifies the TCPC surgical procedure.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This invention is illustrated in the accompanying drawings, throughout which like reference letters indicate corresponding parts in the various figures. The embodiments herein will be better understood from the following description with reference to the drawings, in which.

DETAILED DESCRIPTION OF INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The embodiments herein provide an implantable Flow Streamliner for passively regulating blood streams in a TCPC subject. The implantable Flow Streamliner is configured to separate a blood stream from an IVC and a blood stream from a SVC to circumvent collision between the blood streams. Further, the implantable Flow Streamliner is configured to distribute the blood stream from the IVC, containing hepatic nutrients, in proportion to a LPA and a RPA. Further, the implantable Flow Streamliner is configured to distribute the blood stream from the SVC in proportion to the LPA and the RPA.

Figure 1:
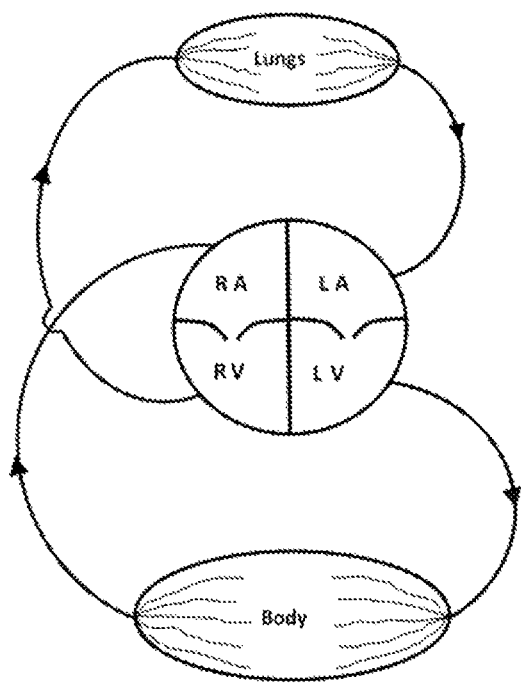
FIG. 1 is a schematic representing a normal blood circulation in a human body.
Figure 2:
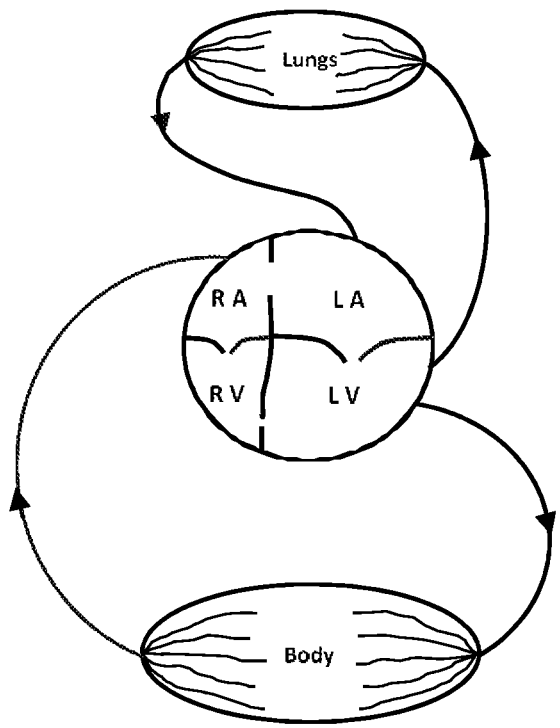
FIG. 2 is a schematic representing a blood circulation in a human body having congenital heart defect with a single ventricle.
Figure 3:
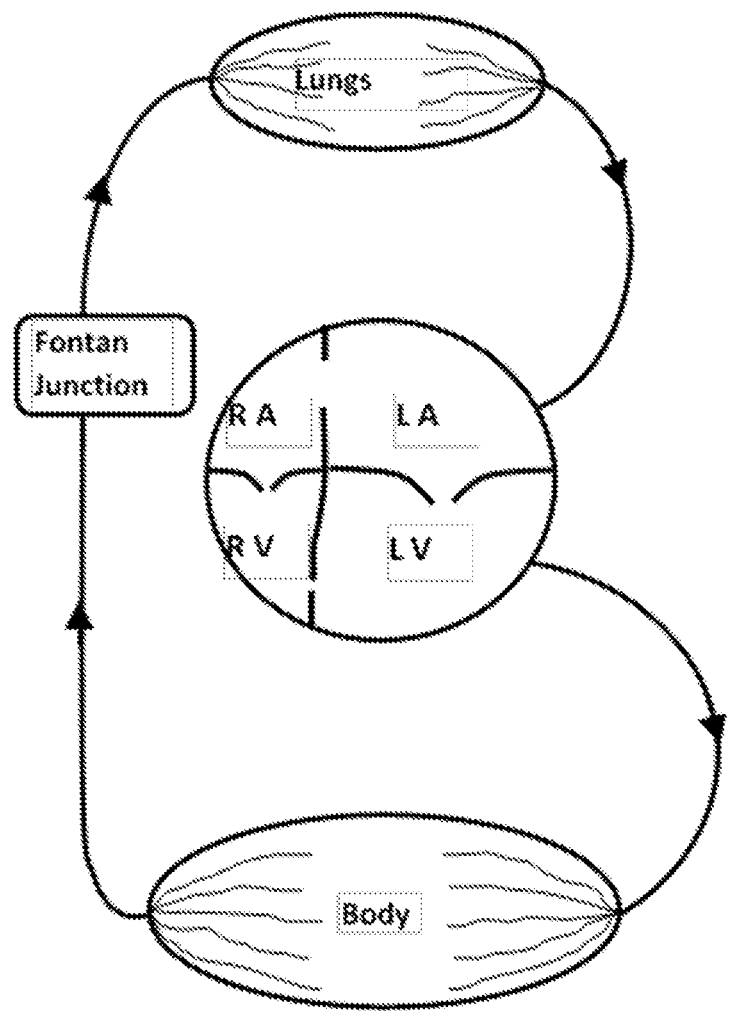
FIG. 3 is a schematic representing a blood circulation in a human body after Fontan surgery.
Figure 4A:
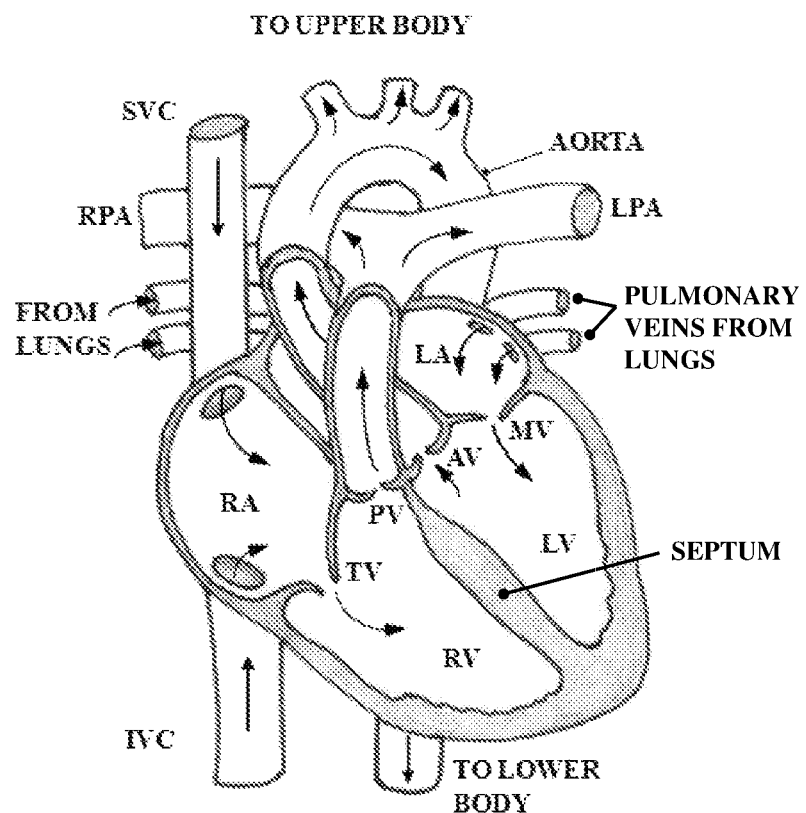
FIGS. 4a-4b illustrate cardiac cross-sectional views of a normal heart and a heart with congenital defect.
Figure 4B:
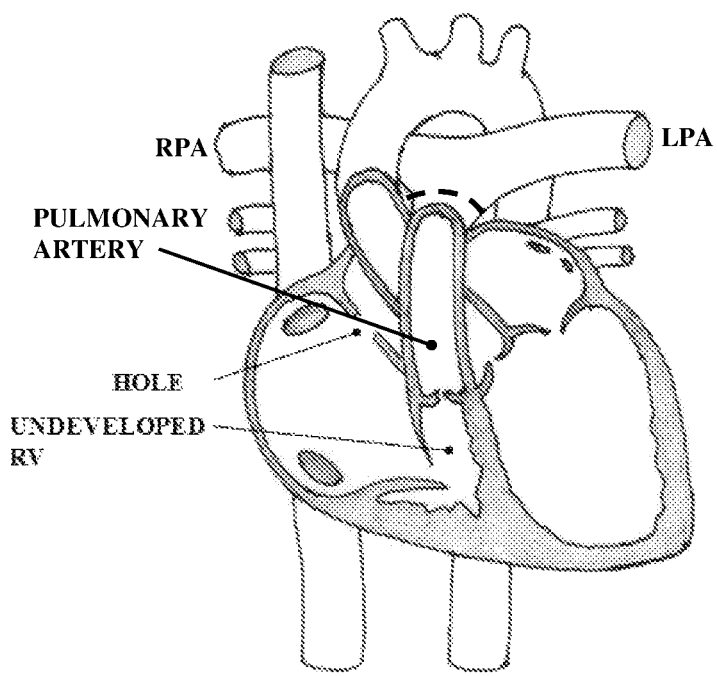

Generally, septum (i.e., wall) of the heart divides the heart vertically into left heart and right heart and each of the left heart and the right heart is further horizontally divided into atrium and ventricle with a non-return valve between them. Thus the heart has four chambers—LA, LV, RA and RV. The RA receives deoxygenated blood from the upper part of the body (head and arms) and lower part of the body (torso and legs) through the SVC and the IVC, respectively. The deoxygenated blood is further supplied through a Tricuspid Valve (TV) to the RV. The RV further pumps the deoxygenated blood through Pulmonary Valve (PV) to the LPA and to the RPA leading to left and right lungs for oxygenation. The LA receives oxygenated blood from the lungs through Pulmonary Veins and pushes the oxygenated blood through Mitral Valve (MV) into the LV. Contraction of the LV pumps the oxygenated blood through Aortic Valve (AV) to highly curved Aorta whose branches supply the oxygenated blood to the upper part of the body and to the lower part of the body, thus completing the circuit of blood circulation as shown in FIG. 4a. The FIG. 4b shows a typical congenital heart defect wherein the RV is malformed and the septum between the RA and the LA has a hole, which allows mixing of the oxygenated blood with the deoxygenated blood. In this scenario the LV alone pumps the mixed blood to the body and to the lungs thereby causing continual deterioration of child's health warranting early surgical treatment.

Figure 5A:
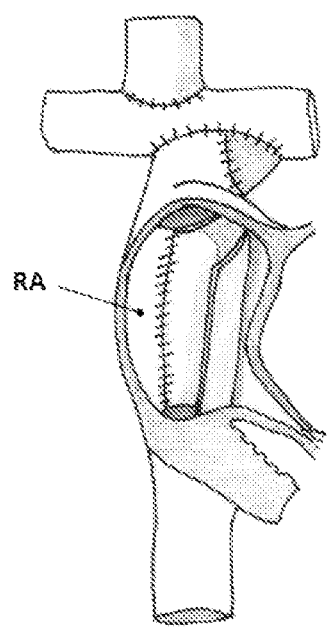
FIGS. 5a-5b illustrate sketches of the TCPC surgery involving construction of a composite intra-atrial tunnel with the use of the posterior wall of the right atrium, and a prosthetic tube connecting the inferior vena cava with the right pulmonary artery from outside the RA.
Figure 5B:
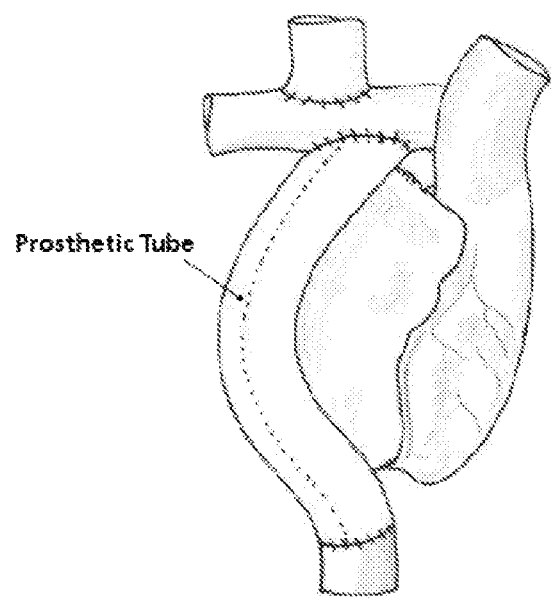

In the conventional methods, a Fontan surgery procedure is the most practiced surgical treatment which includes two variants—Intra-cardiac TCPC (as shown in FIG. 5a) and Extra-cardiac TCPC (as shown in FIG. 5b). In case of the TCPC surgery, a surgeon disconnects the SVC and the IVC from the RA of the heart and joins directly to the RPA to directly return the blood from the body to the lungs. While the Intra-cardiac TCPC involves construction of the composite intra-atrial tunnel with the use of the posterior wall of the RA, the Extra-cardiac TCPC involves extension of the IVC using the prosthetic tube exterior to the RA. Both the TCPC variants present a configuration in the shape of a cross.

Figure 6:
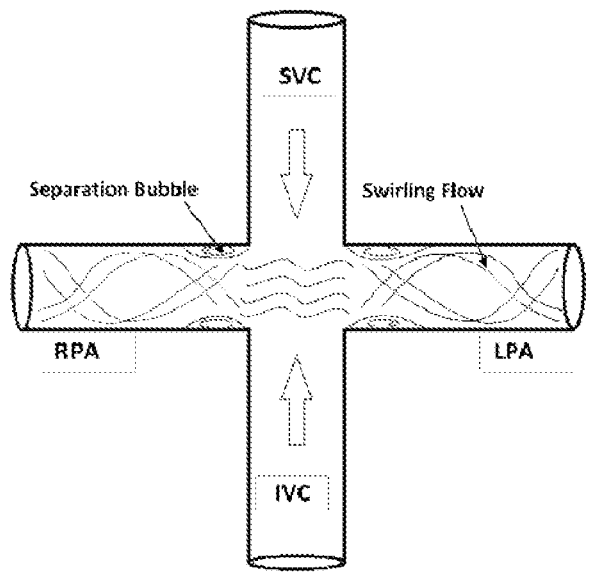
FIG. 6 is a schematic illustrating flow details in a typical TCPC model configuration with co-axial SVC and IVC.

The general flow details in the TCPC model configuration with the co-axial SVC and IVC is depicted in a simplest possible representation of a TCPC junction with flow pattern as shown in the FIG. 6. This configuration of the co-axial SVC and the IVC shows that flows from opposite directions collide with each other within the pulmonary artery which results in loss of momentum, generation of turbulence and swirling flow directed orthogonally into the RPA and the LPA. The flow around sharp corners is marked with separation bubbles which lead to energy loss. The flow separation can be avoided by means of flaring at the joint of tubes which enables smooth turning of the flow.

Figure 7:
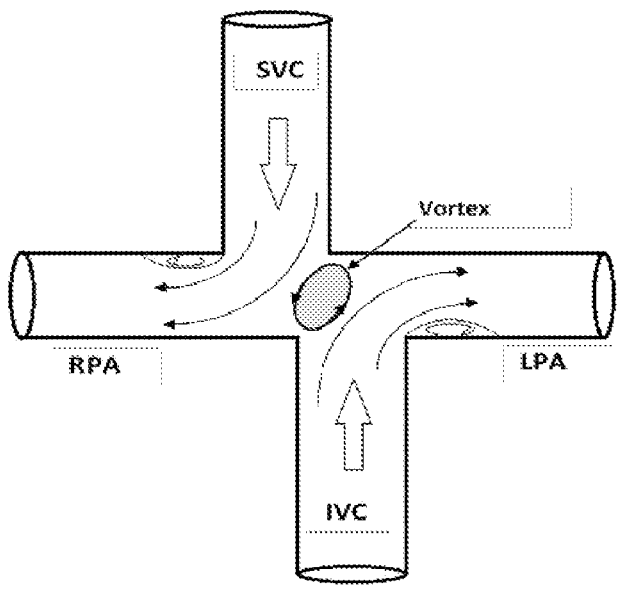
FIG. 7 is a schematic illustrating flow details in a typical TCPC model configuration having SVC and IVC with offset.

In order to circumvent the problems caused by the co-axial SVC and the IVC, surgeons connect the SVC and the IVC to the right pulmonary artery with an offset (as shown in FIG. 7). The offset configuration has been found to reduce the energy loss and therefore this is the currently prevalent surgical practice. However, the offset results in unequal distribution of the blood to the lungs owing to bias of the SVC blood flow towards the RPA and the IVC blood flow towards the LPA which is facilitated by a vortex emerging between these two streams. The presence of the vortex eases friction between two opposite flows from the SVC and the IVC and its rotation is sustained by absorbing the kinetic energy from both the flows. The success of the TCPC with the offset is only partial as one of the two lungs suffers from malformation caused by deprivation of hepatic blood carried by the IVC.

Figure 8A:
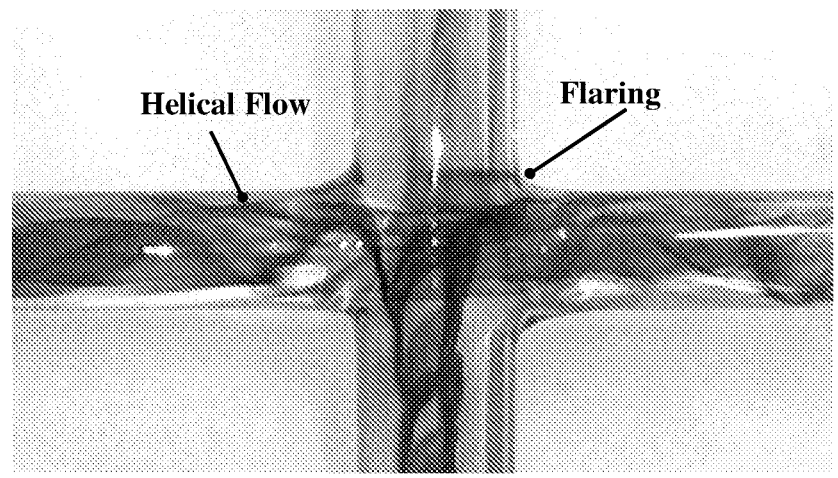
FIGS. 8a-8b illustrate flow visualization carried out experimentally and computationally, respectively in a model of TCPC configuration having co-axial SVC and IVC.
Figure 8B:
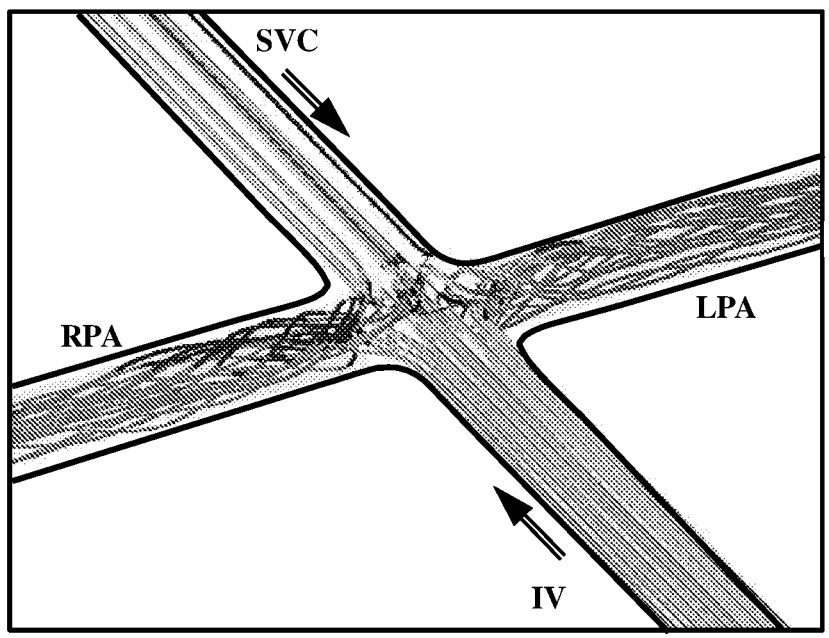

The flow pattern in the TCPC configuration with the SVC and the IVC, being without any offset, was obtained both experimentally and computationally (as shown in FIGS. 8a and 8b). The FIG. 8a shows a picture of streak lines formed by a water flow inside a glass tube model when a color dye is injected in the SVC and the IVC. Due to head on collision of the SVC and the IVC flows in the junction region leads to unsteadiness illustrated by wavy pattern. Further, consequential generation of swirl advecting in the RPA and the LPA is visible in the form of a helical flow (as shown in FIG. 8a). Further, streamlines obtained from the CFD simulation, which also exhibit similar flow features and reaffirms experimental observations are shown in FIG. 8b.

Figure 9A:
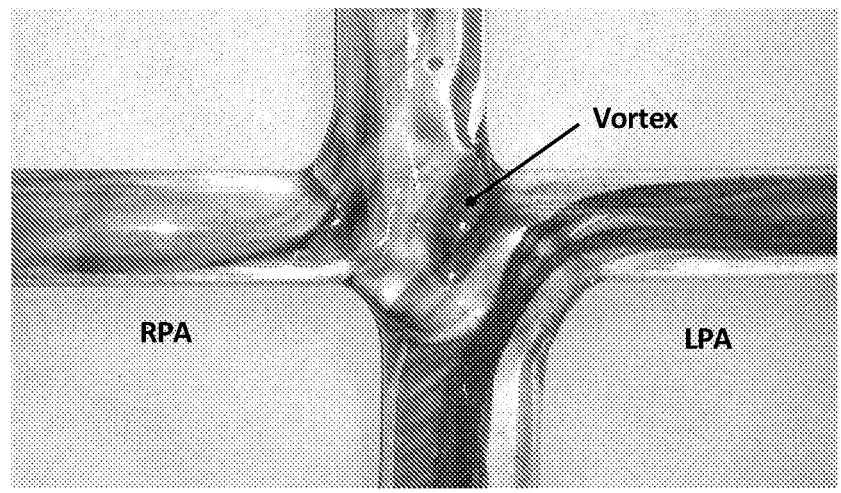
FIGS. 9a-9b illustrate a flow visualization carried out experimentally and computationally in a model of TCPC configuration having SVC and IVC with an offset.
Figure 9B:
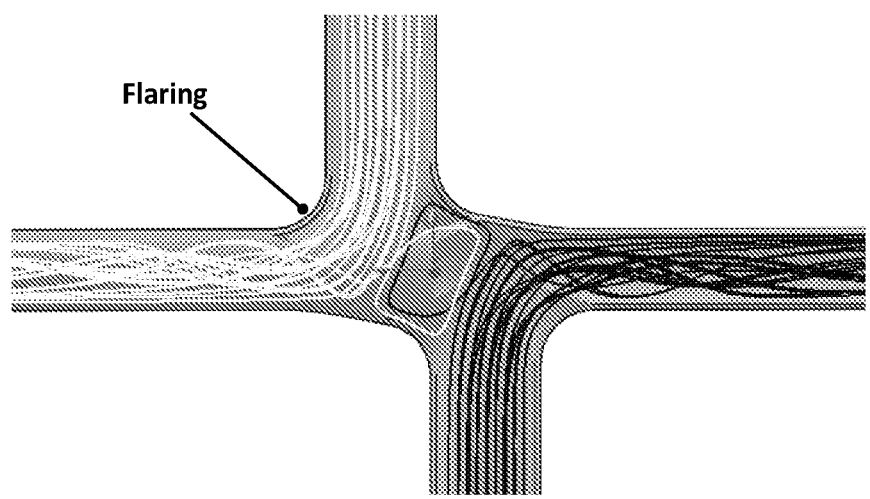

To avoid the head on collision of the SVC and the IVC flows in the junction, an offset is provided between them. Emergence of the flow pattern, shown in FIG. 9a, is obtained from experiments using color dye injection technique in the glass tube model of the TCPC having the offset of about half diameter of the SVC (or IVC as both have equal diameter in the present case). The flow pattern elucidates that if the IVC-RPA joint is on the left of the SVC-RPA joint, most of the flow from the IVC is directed towards the left lung and that from the SVC towards the right lung. The Vortex formation is also prominently visible in the junction as shown in the FIG. 9a. The CFD simulation successfully mimics the experimental results as shown in FIG. 9b where the offset is increased to one diameter which apparently enlarges the vortex and enhances the swirl in the flow towards the lungs.

Figure 10:
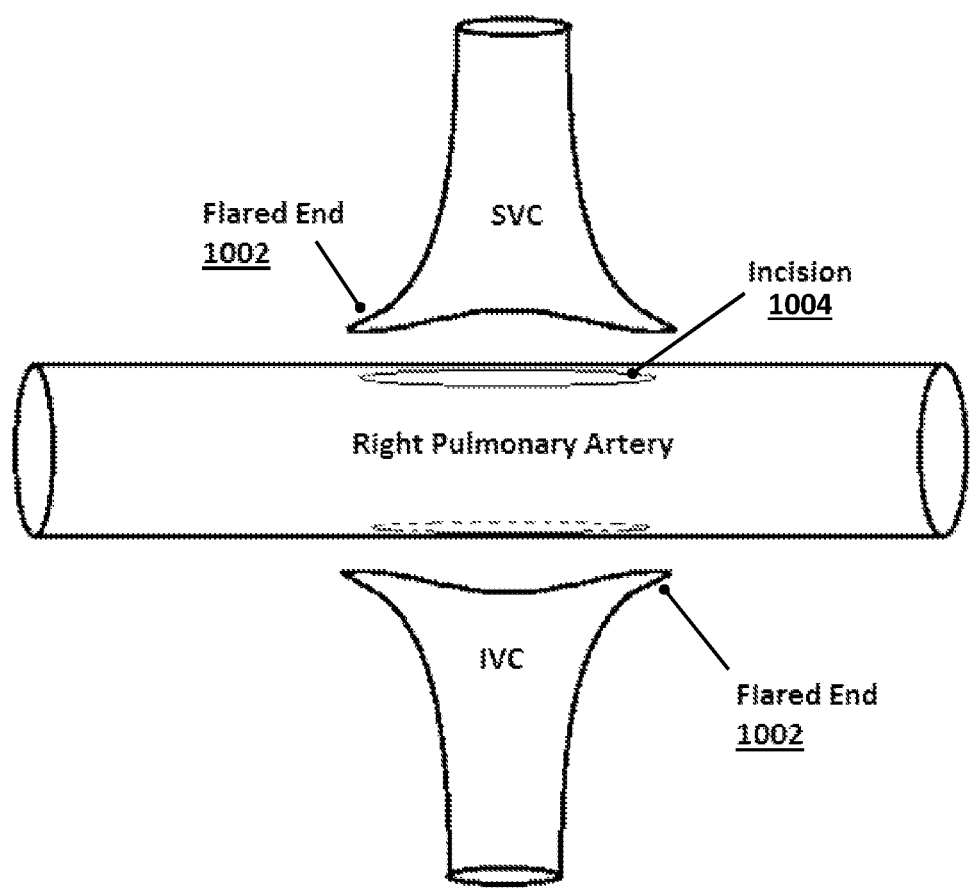
FIG. 10 is a depiction of preparing SVC and IVC with flared ends for connection with right pulmonary artery.

In order to enable smooth turning of flows with suppressed separation, the technique of flared ends 1002 of the SVC and the IVC is used as shown in FIG. 10. Instead of right angled cut, the tube end is flattened and cut in a symmetric wavy shape and stretched over incision 1004 in the right pulmonary artery to make the tube end larger than the diameter of the IVC or the SVC and further sutured accordingly to give flaring 1002.

Unlike the conventional systems and methods, the proposed implantable Flow Streamliner enables smooth flow of the blood streams commencing from the SVC and the IVC equally to the LPA and the RPA. As a result of diminished turbulence due to avoidance of impingement of the two opposite blood streams the energy loss in the blood flow is reduced thereby reducing the load on the ventricle.

Unlike the conventional mechanism, the proposed implantable Flow Streamliner eliminates the need for the offset between the SVC and the IVC and distributes the blood flow equally to both the lungs.

Referring now to the drawings, and more particularly to FIGS. 11 through 18, where similar reference characters denote corresponding features consistently throughout the figures, these are shown in preferred embodiments described herein.

Figure 11:
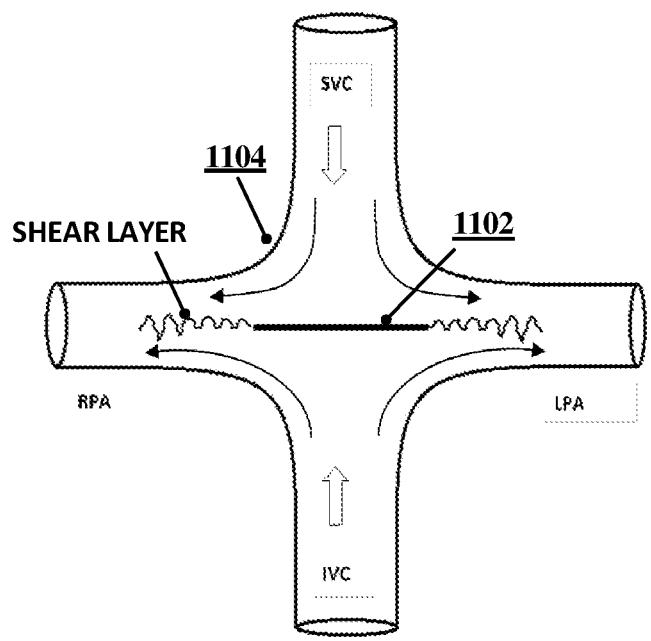
FIG. 11 is a diagram illustrating placement of the implantable Flow Streamliner at the junction between the co-axial SVC and IVC in a typical TCPC configuration, according to an embodiment as disclosed herein.

FIG. 11 is a schematic illustrating the placement of the implantable Flow Streamliner 1102 at the junction between the co-axial SVC and IVC in the TCPC configuration, according to an embodiment as disclosed herein. The implantable Flow Streamliner 1102 is positioned in the junction of the TCPC configuration having the SVC and the IVC without any offset such that their flows approaching from opposite directions are not able to directly see each other. The flows from the SVC and the IVC are diverted by the Flow Streamliner 1102 into the LPA and the RPA.

In an embodiment, the implantable Flow Streamliner 1102 is derived from at least a tissue-engineered material, a biocompatible material, biocompatible polymers, a thin membrane, a flexible (pliable) material, a rigid (stiff) material, a soft material, a hard material in the form of a thin sheet which can be an auto graft, a homograft, a heterograft or the like. In an embodiment, the implantable Flow Streamliner 1102 can be of a patient specific shape and in a patient it can be placed intra-operatively or postoperatively. The patient(s) herein refers, but not limited, to the subject (i.e., human-being, animals, or the like) suffering from the congenital diseases.

In an embodiment, the implantable Flow Streamliner 1102 detailed herein is preferably for the TCPC procedures for the heart, but it will be understood that the implantable Flow Streamliner 1102 can be used in other parts of the body with various blood flows, where the diversion of the blood flow is required. In an embodiment, the subject can be any anatomical flow environments such as the humans, the animals or the like. In an embodiment, the implantable Flow Streamliner can be flat or curved both in two dimensions (2D) and in three dimensions (3D).

The implantable Flow Streamliner 1102 in the pulmonary artery is configured to split the blood stream from the IVC and the blood stream from the SVC to prevent the collision between the blood streams. Further, the implantable Flow Streamliner 1102 is configured to distribute the blood stream from the IVC, containing hepatic nutrients, in proportion to the LPA and the RPA. Further, the implantable Flow Streamliner 1102 is configured to distribute the blood stream from the SVC in proportion to the LPA and the RPA. The implantable Flow Streamliner 1102 prevents the collision between opposite flows from SVC and IVC, thereby inhibiting generation and traveling of turbulent helical flows in the pulmonary arteries. The implantable Flow Streamliner 1102 completely avoids conventional TCPC with offset between the SVC and the IVC and allows their suturing with flared ends onto the pulmonary artery in a cross directly facing each other.

The implantable Flow Streamliner 1102 is a flow control device developed based on the fundamentals of fluid mechanics. Thus, the implantable Flow Streamliner 1102 can be opportunistically utilized in treating the congenital diseases.

Unlike the conventional mechanism, the proposed implantable Flow Streamliner 1102 can simplify the surgery by eliminating the need of creating the offset between the SVC and the IVC. Further, owing to small size of prosthesis, the proposed implantable Flow Streamliner 1102 can mitigate the hindrance to the natural growth of the blood vessels. Furthermore, the proposed implantable Flow Streamliner 1102 can be easily adopted clinically, is minimalist in terms of suturing lines and can be deployed during surgery or even after the surgery.

The provision of the implantable Flow Streamliner 1102 between the two flow paths of the IVC and SVC blood can avoid collision between them and reduce the occurrence of unsteadiness, turbulence and swirl in the blood flowing through the LPA and the RPA.

The ends of the SVC and the IVC are flared (as shown in FIG. 10) which provide flaring 1104 at the joint when sutured to the pulmonary artery. This flaring suppresses the flow separation and enables the blood stream turns smoothly in to the pulmonary artery. In an embodiment, the implantable Flow Streamliner 1102 in which the SVC is connected with the RPA in a flared shaped to enable the blood stream turn smoothly in the LPA. In an embodiment, the implantable Flow Streamliner 1102 in which the SVC is connected with the RPA in the flared shaped to enable the blood stream turn smoothly in the RPA. In an embodiment, the IVC is connected with the RPA in the flared shaped to enable the blood stream turn smoothly in the LPA. The IVC is connected with the RPA in the flared shaped to enable the blood stream turn smoothly in the RPA. The SVC and the IVC are connected with the RPA facing each other. This is the configuration which results in head on collision of the blood streams. However, the proposed implantable Flow Streamliner 1102 placed at the junction in such way that these two streams are not able to directly interact with each other and flow smoothly to LPA and RPA. The flared junctions of SVC and RPA, and IVC and RPA minimize occurrence of the flow separation at the turns.

The blood stream from the IVC, containing hepatic nutrients, is passively regulated in proportion to the LPA and the RPA without constraint. The blood stream from the SVC is passively regulated in proportion to the LPA and the RPA without constraint. The implantable Flow Streamliner 1102 is configured to enable confluence of the blood streams from the SVC and the IVC naturally and smoothly. The implantable Flow Streamliner 1102 is positioned horizontally facing towards the IVC and the SVC, wherein the SVC and the IVC are connected with the RPA facing each other.

In an embodiment, the position of the implantable Flow Streamliner 1102 equalizes the velocity of the blood flow from the IVC and the velocity of the blood flow from the SVC at the LPA while leaving the implantable Flow Streamliner 1102. In an embodiment, the position of the implantable Flow Streamliner 1102 equalizes the velocity of the blood flow from the IVC and the velocity of the blood flow from the SVC at the RPA while leaving the implantable Flow Streamliner 1102. The quantity of blood flow through SVC is about half of that through IVC. Unlike the conventional mechanisms, the implantable Flow Streamliner 1102 ensures equal division of blood flow from each of the SVC and the IVC to both the lungs with minimum energy loss. The equal velocity of two co-flowing streams avoids creation of shear layer(s) and the associated losses.

Unlike the conventional mechanisms, the implantable Flow Streamliner 1102 can be derived from at least a tissue-engineered material, biocompatible polymers, a biocompatible material, an auto graft, a homograft, and a heterograft. Also, the implantable Flow Streamliner is constructed out of thin sheet at least from soft, hard, rigid, a thin membrane, a flexible material, and a rigid material.

The proposed implantable Flow Streamliner 1102 can be used in humans, animals or the like. Further, the implantable Flow Streamliner 1102 can be used in non-anatomical flow environments such as drip irrigation, oil flow in engines, combustion, water pipe lines, and plumbing. The implantable Flow Streamliner 1102 can also be used in non-fluid or flow connections, for example, for electric currents, wave guides and optical connections.

In cases of the patients who had undergone the conventional TCPC surgeries with offset between the SVC and the IVC, the IVC is seen to become curved due to pressure from the RA. The combination of offset and curvature of the IVC creates strong bias in the blood flow and as a result most of the blood from SVC flows to the right lung while the IVC blood carrying hepatic contents flows to the left lung. This configuration needs corrective surgery. In this configuration, the implantable Flow Streamliner 1102 is aligned along the axes of the SVC and the IVC in a curvilinear fashion facing the LPA and the RPA to split each flow into two streams from the SVC and the IVC and guide them to both Right and Left Pulmonary Arteries.

Unlike the conventional method of the TCPC surgery, the implantable Flow Streamliner 1102 eliminates the bias of blood flows from the SVC and the IVC and divide them nearly equally so as to provide hepatic blood to both the lungs.

Unlike the conventional method of the TCPC surgery, the implantable Flow Streamliner 1102 assembly corrects the sharp turn at the junctions of the SVC and the RPA, and the IVC and the RPA by providing flaring 1104 for smooth flow with suppressed separation.

Unlike the conventional method of the TCPC surgery, the implantable Flow Streamliner 1102 can correct the blood vessel geometry having dilation or stenosis or both creating the flow abnormalities. The implantable Flow Streamliner 1102 is implanted by one of routine surgery, minimally invasive surgery and a catheter-based intervention.

Figure 12:
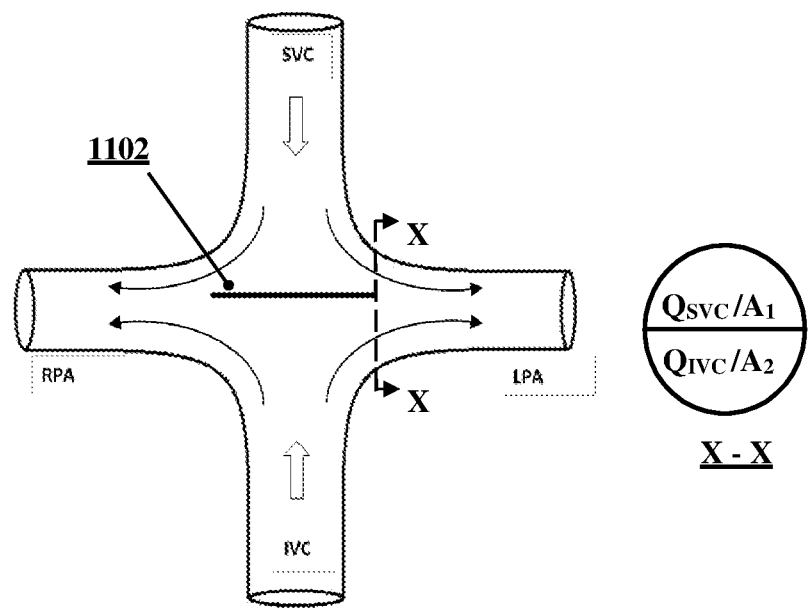
FIG. 12 is a schematic depicting positioning of the implantable Flow Streamliner which divides cross-sectional areas of the LPA and the RPA in proportion to the mass flow rates from the SVC and the IVC, according to an embodiment as disclosed herein.

FIG. 12 is a sketch showing positioning of the implantable Flow Streamliner 1102 which divides cross-sectional area of the pulmonary artery in proportion to the mass flow rates from the SVC and the IVC, according to an embodiment as disclosed herein.

If the co-flowing streams from the SVC and the IVC leave the edges of Flow Streamliner 1102 with different velocities, shear layers are generated at their interface resulting in voracity and turbulence contributing to energy loss. In order to minimize the energy loss owing to the shear, differential velocity across the Flow Streamliner 1102 needs to be reduced (i.e., almost zero). Thus, the Flow Streamliner 1102 is placed in such a way that it divides the cross-sectional area of the pulmonary artery in proportion to the ratio of flow rates from the SVC (QSCV) and the IVC (QIVC). The QSVC and QIVC are the flow rates through the SVC and the IVC. Here, A1 and A2 are areas for streams from the SVC and the IVC, respectively, and the condition (A1/A2)= (QSVC/QIVC) ensures equal velocity of flows across the Flow Streamliner while leaving its edges. The 'X-X' denotes the cross-sectional view of the pulmonary artery at the edge of the implantable Flow Streamliner 1102.

In routine surgery or by minimally invasive surgery or by catheter-based intervention, the implantable Flow Streamliner 1102 can be positioned intra-operatively or postoperatively. The implantable Flow Streamliner 1102 does not impede the natural growth of the blood vessels, aids in evolving the flow splitting in nearly equal amount, and flow merging configuration naturally.

Figure 13:
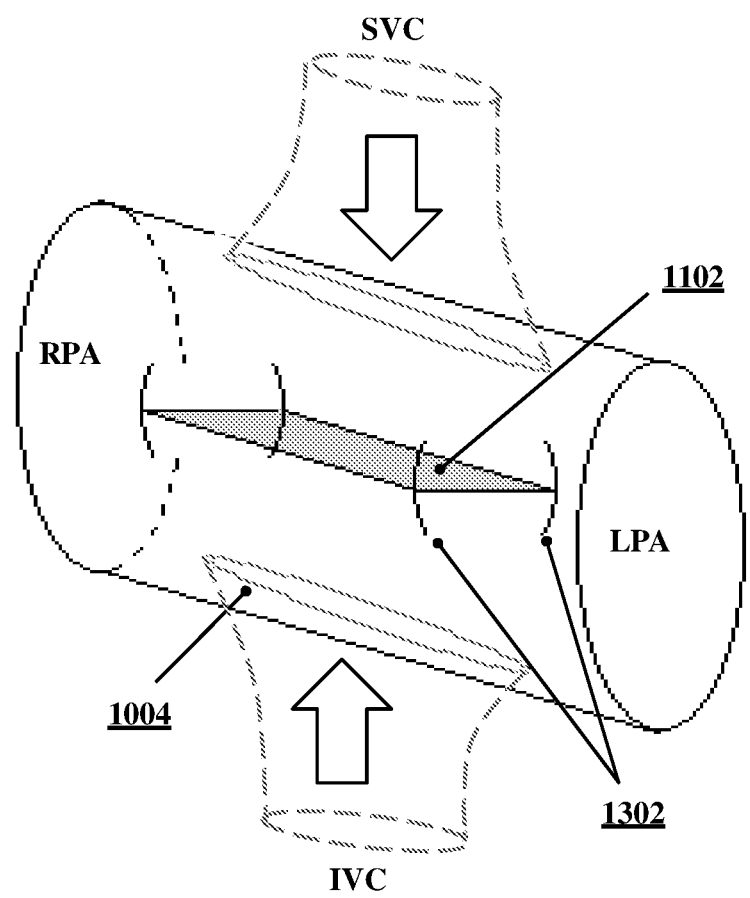
FIG. 13 is a schematic depicting arrangement for fixing the implantable Flow Streamliner in TCPC, according to an embodiment as disclosed herein.

FIG. 13 is a sketch showing arrangement for fixing the implantable Flow Streamliner 1102 in the TCPC, according to an embodiment as disclosed herein. The implantable Flow Streamliner 1102 in the junction is secured with the help of curved clips 1302 (part of the implantable Flow Streamliner 1102 geometry provided at its corners).

In an embodiment, the implantable Flow Streamliner 1102 is positioned horizontally facing towards the IVC and the SVC connected with the RPA facing each other for passively regulating blood streams in a subject. The position of the implantable Flow Streamliner 1102 equalizes the velocity of the blood flow from the IVC and the velocity of the blood flow from the SVC at the LPA while leaving the implantable Flow Streamliner 1102. The position of the implantable Flow Streamliner 1102 equalizes the velocity of the blood flow from the IVC and the velocity of the blood flow from the SVC at the RPA while leaving the implantable Flow Streamliner 1102.

Unlike the conventional mechanisms, the proposed implantable Flow Streamliner 1102 passively regulates the blood streams in the subject. The implantable Flow Streamliner 1102 is further configured to split the blood stream from the IVC and the blood stream from the SVC without the collision between the blood streams. The flared ends of the SVC and the IVC are sutured to the pulmonary artery to allow the growth of the blood vessel by deforming into its shape accordingly.

Unlike the conventional mechanisms, the ends of the SVC and the IVC are flattened and cut in a symmetric wavy shape and stretched over incision 1004 in the RPA to make the tube end larger than the diameter of the IVC or the SVC and further sutured accordingly to give flaring 1104.

Figure 14:
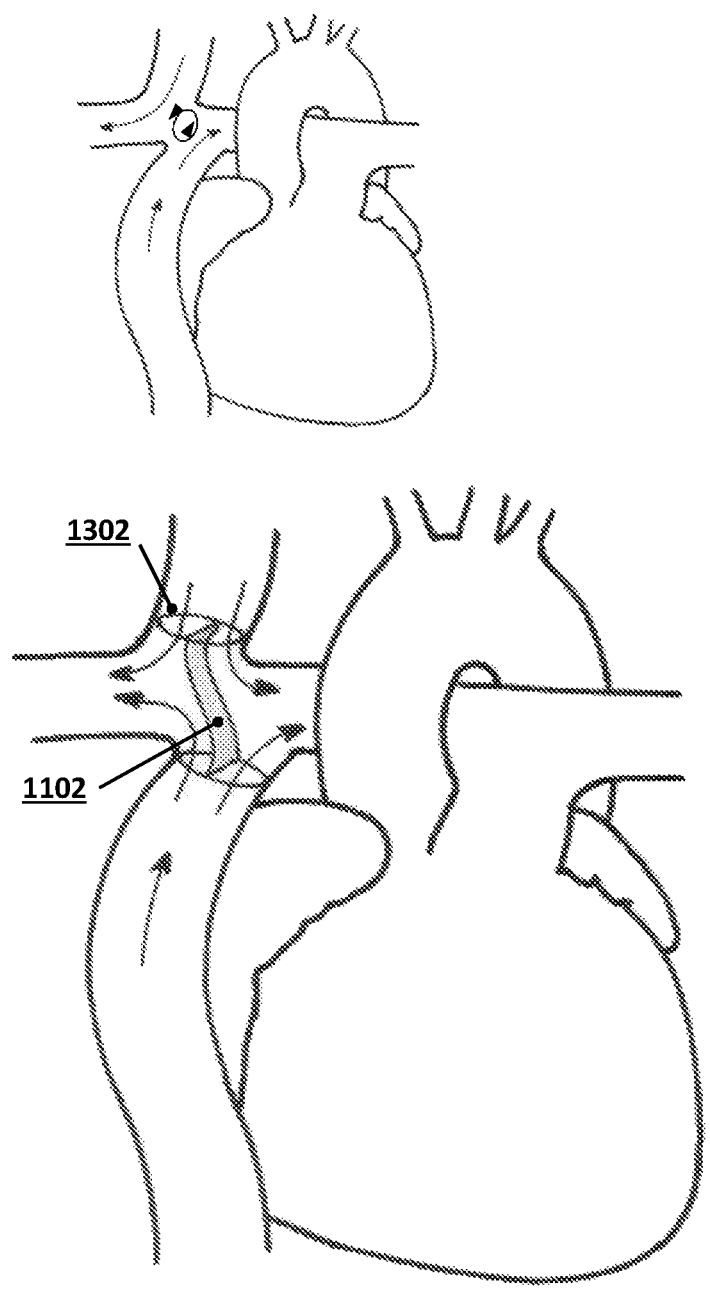
FIG. 14 is a schematic depicting placement of the implantable Flow Streamliner to correct the flow in the existing case of a TCPC with an offset, according to an embodiment as disclosed herein.

The TCPC cases with conventional offset procedure suffer from problem of SVC blood diverting to one lung and IVC blood to another lung thereby hepatic blood not reaching to one of the lungs which consequently develops disorders like pulmonary arteriovenous malformations (PAVMs). Unlike the conventional mechanism, the application of the implantable Flow Streamliner 1102 for correcting such bias in blood flow as shown in FIG. 14. The implantable Flow Streamliner 1102 is implanted to connect the SVC and the IVC smoothly along their axes which diverts the IVC blood flow nearly equally into the RPA and the LPA and similarly the SVC blood flow also gets divided. It will also be possible to implant the Flow Streamliner 1102 with minimally invasive surgery or catheter-based intervention.

Figure 15:
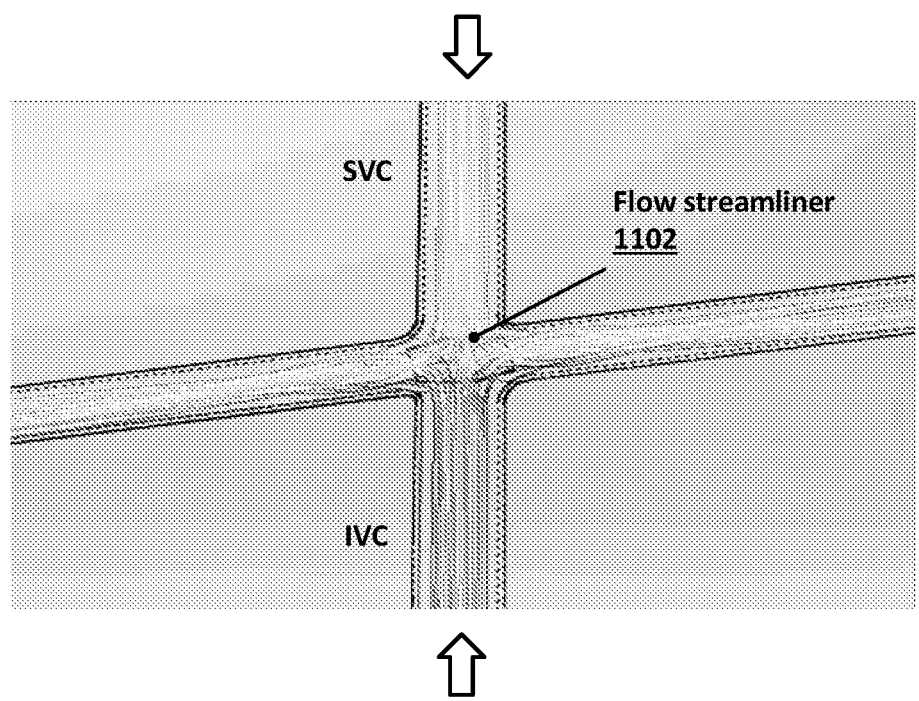
FIG. 15 illustrates a Computational Fluid Dynamics (CFD) simulation which shows suppression of swirling flow in the RPA and the LPA using the implantable Flow Streamliner in the horizontal position in a typical TCPC configuration with the SVC and the IVC without an offset, according to an embodiment as disclosed herein.

FIG. 15 illustrates the CFD simulation illustrating suppression of swirling flow in the pulmonary arteries using the implantable Flow Streamliner 1102 in the TCPC with the co-axial SVC and IVC, according to an embodiment as disclosed herein. The flow pattern is simulated using the CFD in the TCPC model having the co-axial SVC and IVC with the implanted Flow Streamliner 1102 shows that the helical motion of the flows in the LPA and the RPA is considerably suppressed which would reduce the loss of kinetic energy and hence the pressure gets dropped.

Figure 16:
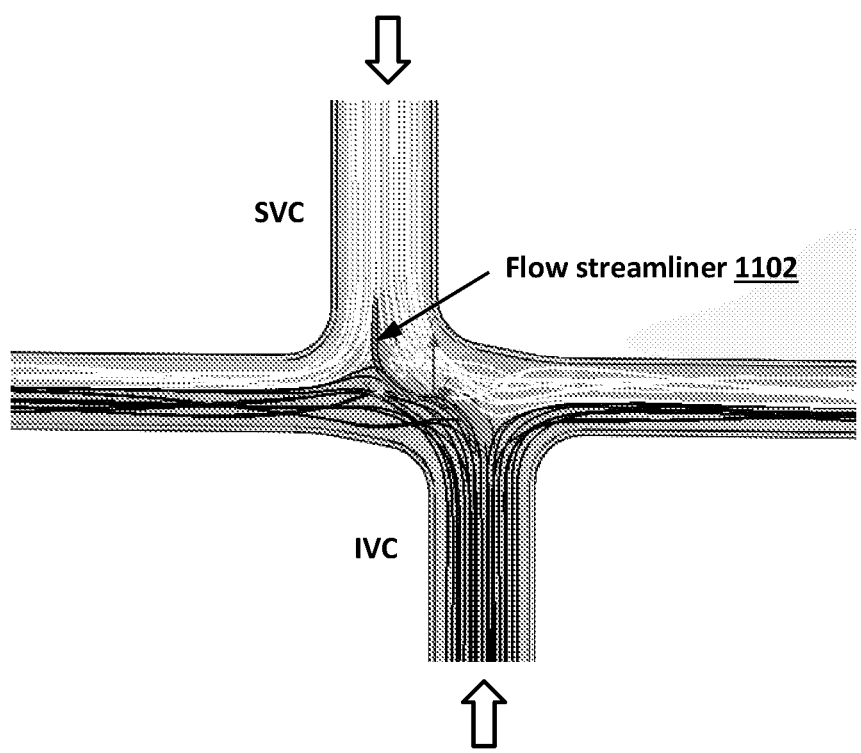
FIG. 16 illustrates the CFD simulation with curvilinear implantable Flow Streamliner in TCPC configuration with offset showing proper diversion of the SVC blood and hepatic blood from the IVC into the LPA and the RPA, according to an embodiment as disclosed herein.

Application of the implantable Flow Streamliner 1102 in the TCPC model with offset is seen to work favorably, wherein the CFD simulation of streamline traces convincingly shows that the flows from the IVC and the SVC are being divided almost equally to both the lungs, as shown in the FIG. 16.

Figure 17:
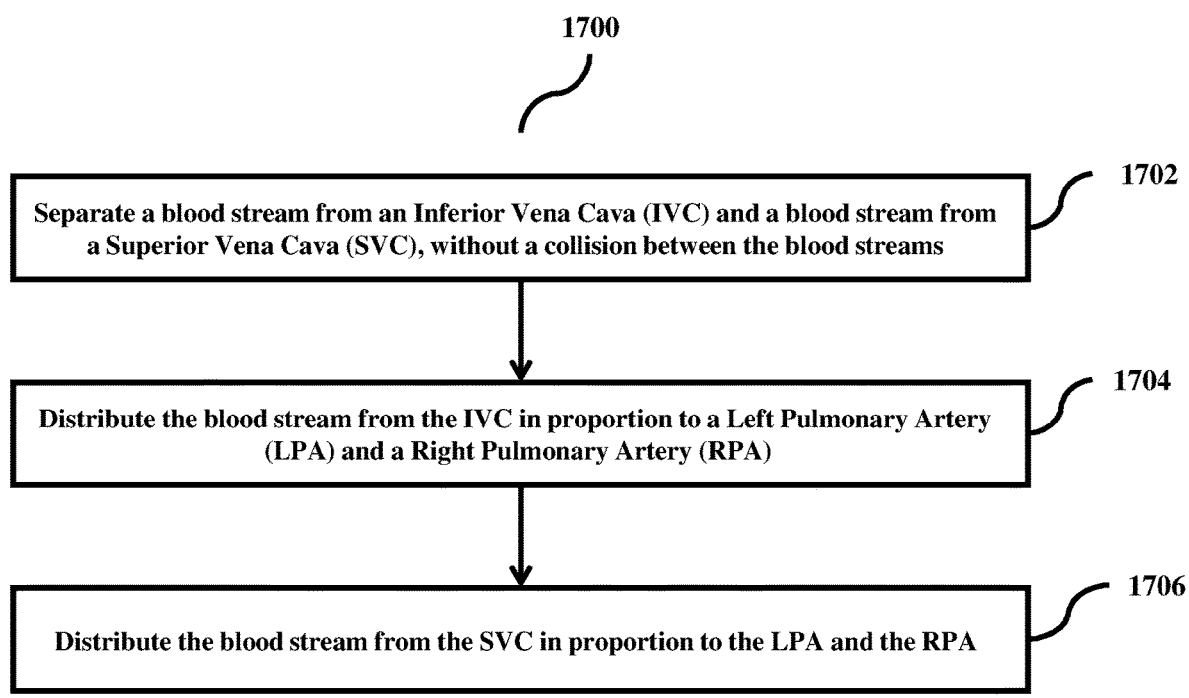
FIG. 17 is a flow diagram illustrating various operations performed by the implantable Flow Streamliner for regulating blood streams in a TCPC subject, according to the embodiment as disclosed herein.

FIG. 17 is a flow diagram 1700 illustrating various operations performed by the implantable Flow Streamliner 1102 for regulating blood streams in a TCPC subject, according to the embodiment as disclosed herein. At step 1702, the implantable Flow Streamliner 1102 is configured to separate the blood stream from the IVC and the blood stream from the SVC, without a collision between the blood streams.

Unlike the conventional mechanisms, the implantable Flow Streamliner 1102 successfully splits the blood stream from the IVC and the blood stream from the SVC without the collision of the blood streams there between. Also the implantable Flow Streamliner 1102 splits the volumetric blood flow to the right and the left lung in proportion with the respective pulmonary vascular impedance, avoiding artificial constraint.

At step 1704, the implantable Flow Streamliner 1102 is configured to distribute the blood stream from the IVC, containing hepatic nutrients, in proportion to the LPA and the RPA.

Unlike the conventional mechanisms, the implantable Flow Streamliner 1102 splits the IVC blood fairly and guide the flow to both lungs hence providing hepatic nutrients to both the lungs ensuring growth of both the lungs without anomalies.

At step 1706, the implantable Flow Streamliner 1102 configured to distribute the blood stream from the SVC in proportion to the LPA and the RPA.

Unlike the conventional mechanisms, the implantable Flow Streamliner 1102 conforms to the new anatomy created by the total cavo-pulmonary connection. Further, the implantable Flow Streamliner 1102 eradicates the need of the offset connection between the IVC and the SVC thereby enabling surgeon to perform simple surgery and avoid more dissections. Furthermore, the implantable Flow Streamliner 1102 avoids the direct head on collision of the blood streams from the SVC and the IVC and reduces momentum loss thereby saving the energy. The implantable Flow Streamliner 1102 can also be extended along the axes of the LPA and the RPA and also the IVC and the SVC.

The foregoing description of the specific embodiments will so fully reveal the general nature of the embodiments herein that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

What is claimed is:

1. An implantable flow streamliner for passively regulating blood streams in a Total Cavo-Pulmonary Connection (TCPC) subject, the implantable flow streamliner comprising:
    a thin pliable sheet having a quadrilateral shape that in at least one of a flat shape in one dimension, a curved shape in two dimensions (2D) and a curved shape in three dimensions (3D);
    wherein the thin pliable sheet is placed in the pulmonary artery such that the thin pliable sheet is at the TCPC junction of the Superior Vena Cava (SVC), the Inferior Vena Cava (IVC), the Left Pulmonary Artery (LPA) and the Right Pulmonary Artery (RPA) while dividing cross-sectional area of the TCPC junction in proportion to mass flow rates of blood streams from the SVC and the IVC to LPA and the RPA,
    wherein the thin pliable sheet bends in a curvilinear manner based on the mass flow rates of the blood streams from the SVC and the IVC to the LPA and the RPA;
    the thin pliable sheet configured to:
        split a blood stream from the Inferior Vena Cava (IVC) and a blood stream from the Superior Vena Cava (SVC), and enable their confluence without a collision between the blood streams and to co-flow without a shear at their interface based on the position of the implantable flow streamliner at the junction of the SVC, the IVC, the LPA and the RPA;
        distribute the blood stream from the IVC, containing hepatic nutrients, in proportion to the LPA and the RPA, eliminating bias of the blood stream from the IVC; and
        distribute the blood stream from the SVC in proportion to the LPA and the RPA, eliminating bias of the blood stream from the SVC.

2. The implantable flow streamliner of claim 1, wherein the implantable flow streamliner is a cardio-vascular flow streamliner.

3. The implantable flow streamliner of claim 1, wherein the blood stream from the IVC, containing the hepatic nutrients, is regulated in proportion to the LPA and the RPA.

4. The implantable flow streamliner of claim 1, wherein the blood stream from the SVC is regulated in proportion to the LPA and the RPA.

5. The implantable flow streamliner of claim 1, wherein the implantable flow streamliner is configured to enable confluence of the blood streams from the SVC and the IVC to the RPA and the LPA.

6. The implantable flow streamliner of claim 1, wherein the implantable flow streamliner is configured to be connected with the SVC and the IVC along their axes having offset.

7. The implantable flow streamliner of claim 1, wherein the implantable flow streamliner is derived from at least one of a tissue-engineered material, biocompatible polymers, a biocompatible material, an auto graft, a homograft, and a heterograft.

8. The implantable flow streamliner of claim 1, wherein the thin pliable sheet is constructed from a biocompatible flexible material.

9. The implantable flow streamliner of claim 1, wherein the flow streamliner has a curvilinear shape adapting to the offset between the SVC and the IVC so as to split the blood streams from the SVC and the IVC into two blood streams and guide them to the RPA and the LPA.

10. The implantable flow streamliner of claim 1, wherein the implantable flow streamliner corrects irregularity in the TCPC configuration in the form of at least one of dilation and stenosis creating flow abnormalities.

11. The implantable flow streamliner of claim 1, wherein the implantable flow streamliner is implanted by one of a minimally invasive surgery and a catheter-based intervention for correcting the flow abnormalities in old TCPC subjects.

12. The implantable flow streamliner of claim 1, wherein the implantable flow streamliner allows natural growth of the blood vessels.

13. The implantable flow streamliner of claim 1, wherein the implantable flow streamliner is implanted to reduce the energy loss and improve the cardio-vascular hemodynamics in the TCPC subject.

* * * * *